US012735753B2

(12) United States Patent
Hu et al.

(10) Patent No.: US 12,735,753 B2
(45) Date of Patent: Sep. 15, 2026

(54) CRISPR-BASED ASSAY FOR DETECTING TB IN BODILY FLUIDS

(71) Applicant: The Administrators of the Tulane Educational Fund, New Orleans, LA (US)

(72) Inventors: Tony Ye Hu, New Orleans, LA (US); Bo Ning, New Orleans, LA (US); Zhen Huang, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 857 days.

(21) Appl. No.: 17/797,425

(22) PCT Filed: Feb. 5, 2021

(86) PCT No.: PCT/US2021/016931
§ 371 (c)(1),
(2) Date: Aug. 3, 2022

(87) PCT Pub. No.: WO2021/159000
PCT Pub. Date: Aug. 12, 2021

(65) Prior Publication Data

US 2023/0087018 A1 Mar. 23, 2023

Related U.S. Application Data

(60) Provisional application No. 62/971,210, filed on Feb. 6, 2020.

(51) Int. Cl.
*C12Q 1/689* (2018.01)
*C12N 15/10* (2006.01)
*C12Q 1/686* (2018.01)

(52) U.S. Cl.
CPC ......... *C12Q 1/689* (2013.01); *C12N 15/1003* (2013.01); *C12Q 1/686* (2013.01); *C12N 2310/20* (2017.05)

(58) Field of Classification Search
CPC .... C12Q 1/689; C12Q 1/686; C12N 15/1003; C12N 2310/20; A61P 37/08; A61K 39/35; C07K 14/35
See application file for complete search history.

(56) References Cited

U.S. PATENT DOCUMENTS

| | | | |
|---|---|---|---|
| 2014/0113305 | A1 | 4/2014 | Schorey |
| 2016/0115471 | A1 | 4/2016 | Kim |
| 2017/0247747 | A1 | 8/2017 | Alland |

FOREIGN PATENT DOCUMENTS

| | | | | |
|---|---|---|---|---|
| CN | 109811072 | A | * | 5/2019 |
| CN | 110541022 | A | | 11/2022 |
| JP | 2004536596 | 1 | | 12/2004 |
| JP | 2017530710 | A | | 10/2017 |
| RU | 2163638 | C | * | 2/2001 |
| WO | 2002101353 | A2 | | 12/2002 |
| WO | 2016057905 | A1 | | 4/2016 |
| WO | WO 2017207825 | | * | 12/2017 |
| WO | 2018170340 | A1 | | 9/2018 |
| WO | 2019104058 | A1 | | 11/2018 |
| WO | 02101353 | A3 | | 12/2022 |

OTHER PUBLICATIONS

English translation.*

For.*

Fernandez-Carballo et al., Journal of Clinical Microbiology, 57(4), e01234-18, Apr. 1-10, (Year: 2019).*

Office Action for Japanese application No. 2 0 2 2 - 5 4 7 8 4 8 dated Apr. 30, 2025.

Extended European Search report for Application EP21750130 dated Mar. 13, 2024.

Shell, S. S.; Prestwich, E. G.; Baek, S-H.; Shah, R. R.; Sassetti, C. M.; Dedon, P. C.; Fortune, S. M. “DNA methylation impacts gene expression and ensure hypoxic survival of *Mycobacterium tuberculosis.*” (2013) PLOS Pathogens, vol. 9, Issue 7, e1003419.

Invitrogen AccuPrimeTM Pfx DNA Polymerase™Product Information Sheet.

Ai, J-W.; Zhou, X.; Xu, T.; Yang, M.; Chen, Y.; He, G-Q.; Pan, N.; Cai, Y.; Li, Y.; Wang, X.; Su, H.; Wang, T.; Zeng, W.; Zhang, W-H. “CRISPR-based rapid and ultra-sensitive diagnostic test for *Mycobacterium tuberculosis.*” (2019) Emerging Microbes & Infections, vol. 8, pp. 1361-1369.

Jing-Wen Ai, et al “CRISPR-based rapid and ultra-sensitive diagnostic test for *Mycobacterium tuberculosis*” Emerging Microbes & Infections (2019) , 8: 1361-1369.

Shell, Scarlet S. “DNA Methylation Impacts Gene Expression and Ensures Hypoxic Survival of *Mycobacterium tuberculosis*” PLOS Pathog (2013) 9 (7) : 1-15.

AccuPrime Pfc DNA Polymerase Product Information Sheet, May 2016.

Fernandez-Carballo, et al. “Toward the Development of Circulating Free DNA-Based In Vitro Diagnostic Test for Infectious Diseases: a Review of Evidence for Tuberculosis.” Journal of Clinical Microbiology. 2019. 57 (4) : 1-9.

(International Preliminary Report on Patentability—IPRP)—PCT/US2021/016931.

Ai et al., CRISPR-based rapid and ultra-sensitive diagnostic test for Mycobacterium tuberculosis. Emerging Microbes & Infections, 2019, vol. 8, No. 1, p. 1361-1369. Abstract; p. 1362, col. 1, para 2; col. 2, para 5; p. 1363, col. 1, para 1-3; col. 2, para 4; p. 1364, Figure 1 legend; p. 1367, col. 1, para 1.

(Continued)

*Primary Examiner* — Cynthia B Wilder
(74) *Attorney, Agent, or Firm* — Thomas | Horstemeyer LLP.

(57) ABSTRACT

The present disclosure describes a method for detecting the presence of *Mycobacterium tuberculosis* in a bodily fluid sample. The method utilizes CRISPR effector proteins along with a guide RNA and a reporter molecule, such that when the guide RNA hybridizes with a target nucleotide fragment, the CRISPR effector protein cleaves the reporter molecule, resulting in a detectable signal.

20 Claims, 1 Drawing Sheet

Specification includes a Sequence Listing.

(56) References Cited

OTHER PUBLICATIONS

Shell et al., DNA Methylation Impacts Gene Expression and Ensures Hypoxic Survival of Mycobacterium tuberculosis. PLoS Pathog, Jul. 4, 2013, vol. 9, No. 7, e1003419, p. 1-15. Abstract.
Invitrogen Product Information Sheet AccuPrime Pfx DNA Polymerase. May 5, 2016 [online]. [Retrieved on Apr. 30, 2021]. Retrieved from the internet <URL: http://tools.thermofisher.com/contenVsfs/manuals/accuprimepfx_man.pdf>, Entire document.
Indonesian Office Action in Application No. HKI-3-KI.05.01.08-TL-II-P00202209444 dated Jun. 17, 2026.

* cited by examiner

FIGURE 1
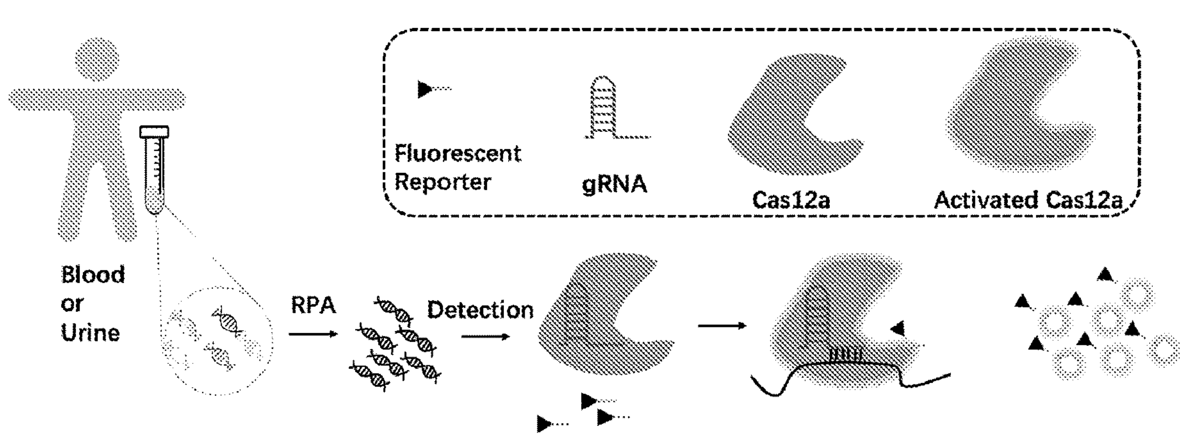
FIGURE 2
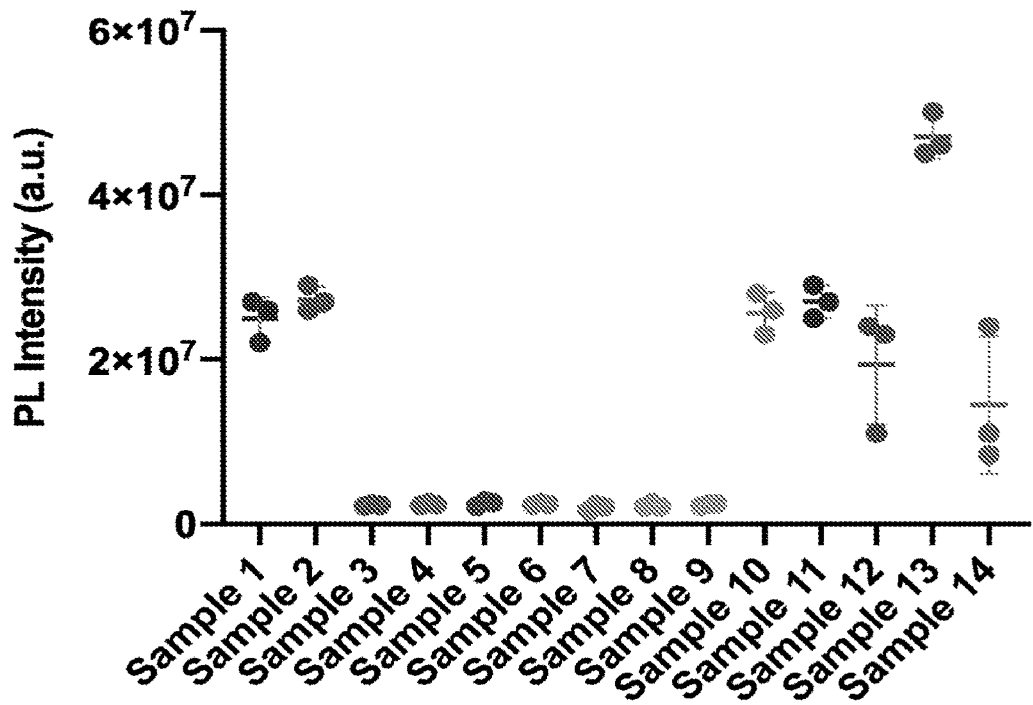

SEQUENCE LISTING

```
<160> NUMBER OF SEQ ID NOS: 9

<210> SEQ ID NO 1
<211> LENGTH: 31
<212> TYPE: DNA
<213> ORGANISM: Artificial Sequence
<220> FEATURE:
<223> OTHER INFORMATION: Synthesized PCR primer

<400> SEQUENCE: 1

ggtcggaagc tcctatgaca atgcactagc c                                31


<210> SEQ ID NO 2
<211> LENGTH: 30
<212> TYPE: DNA
<213> ORGANISM: Artificial Sequence
<220> FEATURE:
<223> OTHER INFORMATION: Synthesized PCR primer

<400> SEQUENCE: 2

ttgagcgtag taggcagcct cgagttcgac                                  30


<210> SEQ ID NO 3
<211> LENGTH: 31
<212> TYPE: DNA
<213> ORGANISM: Artificial Sequence
<220> FEATURE:
<223> OTHER INFORMATION: Synthesized PCR primer

<400> SEQUENCE: 3

taaagagaga aagtagtcca gcatggcaga g                                31


<210> SEQ ID NO 4
<211> LENGTH: 30
<212> TYPE: DNA
<213> ORGANISM: Artificial Sequence
```

-continued

<220> FEATURE:
<223> OTHER INFORMATION: Synthesized PCR primer

<400> SEQUENCE: 4
tctcgtcgag ttcctgcttc tgcttattgg 30

<210> SEQ ID NO 5
<211> LENGTH: 31
<212> TYPE: DNA
<213> ORGANISM: Artificial Sequence
<220> FEATURE:
<223> OTHER INFORMATION: Synthesized PCR primer

<400> SEQUENCE: 5
ctgttgttga cgttgttgtt ccggttcatg c 31

<210> SEQ ID NO 6
<211> LENGTH: 31
<212> TYPE: DNA
<213> ORGANISM: Artificial Sequence
<220> FEATURE:
<223> OTHER INFORMATION: Synthesized PCR primer

<400> SEQUENCE: 6
ctgaatgccg tcttccttgt tgatcttctt c 31

<210> SEQ ID NO 7
<211> LENGTH: 40
<212> TYPE: RNA
<213> ORGANISM: Artificial Sequence
<220> FEATURE:
<223> OTHER INFORMATION: gRNA sequence

<400> SEQUENCE: 7
uaauuucuac ucuuguagau aucagcucgg ucuugaauag 40

<210> SEQ ID NO 8
<211> LENGTH: 40
<212> TYPE: RNA
<213> ORGANISM: Artificial Sequence
<220> FEATURE:
<223> OTHER INFORMATION: gRNA sequence

<400> SEQUENCE: 8
uaauuucuac ucuuguagau gagcggaucu ccggcgaccu 40

<210> SEQ ID NO 9
<211> LENGTH: 40
<212> TYPE: RNA
<213> ORGANISM: Artificial Sequence
<220> FEATURE:
<223> OTHER INFORMATION: gRNA sequence

<400> SEQUENCE: 9
uaauuucuac ucuuguagau gcacaaccgc cgcuguacaa 40

CRISPR-BASED ASSAY FOR DETECTING TB IN BODILY FLUIDS

PRIOR RELATED APPLICATIONS

The application is a National Phase filing under 35 U.S.C. § 371 of International Application PCT/US21/16931, filed on Feb. 5, 2021, which claims priority to U.S. Ser. No. 62/971,210, filed Feb. 6, 2020, and each of which is incorporated by reference herein in its entirety for all purposes.

FEDERALLY SPONSORED RESEARCH STATEMENT

Not applicable.

FIELD OF THE DISCLOSURE

The disclosure generally relates to a method of detecting tuberculosis (TB) in circulating fluids, such as serum, plasma, urine and cerebrospinal fluid (CSF), and more particularly relates to a method of detecting tuberculosis in serum using CRISPR-based reporter system.

BACKGROUND OF THE DISCLOSURE

Tuberculosis (TB) is a serious disease that affects millions of people each year, and is among the top 10 causes of death worldwide. Delay in diagnosis can lead to death. While sputum samples are primarily used to diagnose pulmonary TB, some patients are not able to expectorate sputum, for example those that are very sick or very young.

Currently TB diagnosis relies on Xpert MTB/RIF® (a test that simultaneously detects *Mycobacterium tuberculosis* complex (MTBC) and resistance to rifampin (RIF)), which requires a sputum sample. Although the bacteria load is high in sputum, it can be difficult to collect as a sample. Additionally, sputum may not be collected from every TB patient, especially for extrapulmonary TB patients, and extrapulmonary TB (EPTB) is common, especially in HIV patients.

Blood is an alternative candidate for TB detection, especially in HIV-infected patients, for it is easier and more reliable to collect than sputum. However, *Mycobacterium tuberculosis* is rarely detected by blood test. TB blood culture could take several weeks to become positive and requires facilities with certain equipment. Nucleic acid amplification tests are less than ideal with blood due to low sensitivity (20-55%), possibly because of the low bacteria load, the presence of PCR inhibitors or small volume of samples typically employed for these tests.

Therefore, there is the need for a highly sensitive serum test for tuberculosis that has high specificity.

SUMMARY OF THE DISCLOSURE

The present disclosure describes a method for detecting *Mycobacterium tuberculosis* ("MTB") in a serum sample. Please refer to FIG. 1, which illustrates the method of this disclosure. In the first step, nucleic acids are extracted from the sample, such as a serum sample. The nucleic acid is then amplified targeting an MTB-specific sequence, if present. The product of amplification is then reacted with a gRNA-CRISPR system along with a reporter molecule. If the MTB-specific sequence is present, the gRNA will hybridize with it to activate the CRISPR effector protein, which then cleave the reporter molecule and one can determine the presence of MTB based on measurement of signals produced by the reporter molecule.

CRISPR (Clustered Regularly Interspaced Short Palindromic Repeats) is a family of DNA sequences found within the genomes of prokaryotic organisms such as bacteria and archaea. These sequences are derived from DNA fragments of bacteriophages that have previously infected the prokaryote and are used to detect and destroy DNA from similar phages during subsequent infections, and therefore they serve as an important part of the prokaryotes' immune system.

CRISPR-associated protein 9 ("Cas9") is an enzyme that uses CRISPR sequences as a guide to recognize and cleave specific strands of DNA that are complementary to the CRISPR sequence. The Cas9 endonuclease is a four-component system that includes two small crRNA molecules and trans-activating CRISPR RNA (tracrRNA). The two RNA sequences were fused into a single guide RNA (gRNA), which guides Cas9 to find and cut the DNA target specified by the guide RNA. Cas9 enzymes together with CRISPR sequences form the basis of a technology known as CRISPR-Cas9 that can be used to edit genes within organisms. By manipulating the nucleotide sequence of the guide RNA, the artificial Cas9 system could be programmed to target any DNA sequence for cleavage.

Nuclease Cas12a (formerly known as Cpf1), another member of the Cas family, showed several key differences from Cas9 including: causing a 'staggered' cut in double stranded DNA as opposed to the 'blunt' cut produced by Cas9, relying on a 'T rich' protospacer adjacent motifs, thus providing alternative targeting sites to Cas9, and requiring only one CRISPR RNA for successful targeting.

Cas13 (including four subtypes: Cas13a-d) functions similarly to Cas9, using a ~64-nt guide RNA to encode target specificity. The Cas13 protein complexes with the guide RNA via recognition of a short hairpin in the crRNA, and target specificity is encoded by a 28 to 30-nt spacer that is complementary to the target region. In addition to programmable RNase activity, all Cas13s exhibit collateral activity after recognition and cleavage of a target transcript, leading to non-specific degradation of any nearby transcripts regardless of complementarity to the spacer.

In one embodiment, the CRISPR effector protein is Cas12a (formerly known as Cpf1), Cas9 or Cas13. However, other CRISPR effector proteins can be used, as long as effective detection with high specificity can be achieved.

By properly designing the gRNA by varying its length and location in a particular gene, one can thus target a DNA fragment with the desirable specificity and sensitivity. Therefore, with the CRISPR-Cas-gRNA method of this disclosure, highly sensitive and specific detection of MTB in serum can be achieved in a matter of hours. It is expected to be able to detect a single copy of MTB DNA in a 5 μl of serum sample.

The method can also be used to distinguish MTB and nontuberculous mycobacteria (NTM), and identify *Mycobacterium* species by targeting species-specific DNA fragments. NTM infection has similar symptoms to those produced by MTB, while over 150 different species of NTM have been described, the identification of these organisms in pulmonary specimens does not always equate with active infection. Supportive radiographic and clinical findings are needed to establish the diagnosis, and treating or eradicating NTM infections has been challenging.

Further variation can be carried out in order to enhance MTB detection. In one embodiment, the DNA extracted from the serum sample can be further enriched by first treated with anti-DNA antibodies. In another embodiment, the DNA extracted from the serum sample can be further treated with anti-human DNA antibodies in order to deplete human DNA from the sample.

In one embodiment, anti-human DNA antibody is anti-5-methylcytidine (5mC) antibody. However, other antibodies or proteins can be used, as long as it can bind to methylated DNA, such as anti-CpG DNA methylation, include 5-methylcytidine (5-mC) 5-hydroxymethyl-(5-hmC), 5-formyl-(5-fC) and 5-carboxy- (5-caC) cytosine antibodies; CpG DNA methylation binding proteins, methyl-CpG binding domain (MBD) proteins: MeCP2, MBD1, MBD2, MBD3, MBD4, MBD5, MBD6, TET1, TET2, TET3, Kaiso and their antibodies; as well as methylated RNA, such as anti-N7-methylguanosine (m7G), 5-methylcytidine (5mC) and its oxidized form 5-hydroxylmethylcytidine (5hmC), N6-methyladenosine (m6A), N1-methyladenosine (m1A), pseudouridine (Ψ) and inosine (I) RNA antibodies; and methyl-RNA binding proteins METTL3, METTL14, FTO, ALKBH5, YTHDF1, YTHDF2, YTHDC1, ZNF217 and their antibodies.

Further enrichment can be achieved by isolating extracellular vesicles (EVs) prior to amplification. EVs are small membranous vesicles originating from the endosomal cell compartment when multi-vesicular bodies fuse with the plasma membrane. Secreted EVs are relatively stable and act as effective carriers of proteins, polypeptides, genes, soluble factors and membrane-bound receptors/ligands from a parent cell/bacterium, and therefore EVs isolated by ultracentrifuge from human serum or plasma can increase MTB DNA or RNA yield.

To isolate EVs, ultracentrifugation of greater than 100,000 g (42,000 rpm) is generally practiced. However, a person skilled in the art would appreciate other methods to isolate EVs, such as density-gradient separation, polymer-based precipitation, immunological selection, microfluidic isolation, size exclusion chromatography, membrane filtration, membrane affinity isolation.

Density-gradient separation refers to a method of loading samples onto sucrose solutions of different density profiles followed by ultracentrifugation, such that the EVs can be separated from protein aggregates and other impurities. For example, density gradient ultracentrifugation can be performed by loading plasma sample onto 50, 30, and 10% iodixanol layers and then centrifuged at 120,000×g for 24 hours. Ten fractions (F1-10) are collected from top to bottom, in which the ones with highest EVs content can then be further purified.

Polymer-based precipitation includes mixing the biological sample with polymer-containing precipitation solution, followed by incubation and centrifugation at low speed. One of the most common polymers used is polyethylene glycol.

Immuno-selection techniques use antibody-based separation methods targeting known surface markers on extracellular vesicles. Some of these markers include the well characterized tetraspanins (CD9, CD63, CD81) or immune-regulator molecules (MHC I&II) on the surface of the vesicles.

Microfluid isolation are based on trapping EVs in micro channels, and can be an option for low volume input of biofluids.

Size-exclusion chromatography is used to separate macromolecules on the base of size, not molecular weight. The technique applies a column packed with porous polymeric beads containing multiple pores and tunnels. The molecules pass through the beads depending on their diameter. It takes a longer time for molecules with small radii to migrate through pores of the column, while macromolecules elute earlier from the column. Size-exclusion chromatography allows precise separation of large and small molecules. Moreover, different eluting solutions can be applied to this method.

Membrane filtration can also be used for isolation of exosomes. Depending on the size of microvesicles, this method allows the separation of EVs from proteins and other macromolecules. EVs may also be isolated by trapping them via a porous structure. In particular, a micropillar porous silicon ciliated structure was designed to isolate 40-100 nm EVs. In addition to the standard filtration techniques, tangential flow filtration can also be used for effective isolation of EVs. This method is used for isolation of EVs with well-determined size by removing free peptides and other small compounds.

Various DNA amplification techniques can be used, as each technique has its advantages and disadvantages. The method of this disclosure can employ the common DNA amplification techniques, such as PCR, RPA, RCA, LAMP, etc., as well as any newly developed amplification methods.

The methods combine amplification and CRISPR detection. In amplification steps, hybridization enhancer component in reaction buffer can be used to enhance specific primer-template hybridization during every cycle of DNA amplification, preventing mispriming and improving DNA amplification specificity and yield. We expect to be able to amplify MTB DNA from a single copy in 5 μl of serum sample for CRISPR detection.

Hybridization enhancers can be further carried over to the CRISPR detection step, as they can further improve hybridization between of guide RNA and target sequences and reduce mismatch. Such enhancers are expected to be able to stabilize and enhance activities of CRISPR proteins and amplify signal.

In one embodiment, the hybridization enhancers are the thermostable AccuPrime accessory proteins. These enhance specific primer-template hybridization during every cycle of PCR, preventing mispriming and improving PCR specificity and yield. Other hybridization enhancers can also be used, as long as they can enhance specificity of hybridization. Non-limiting examples of hybridization enhancers include anionic polymers, in situ hybridization buffers and similar buffer components, AccuPrime accessory proteins, ULTRAhyb™ Ultrasensitive Hybridization Buffer and the like.

As used herein, "CRISPR proteins" or "CRISPR effector protein" or "CRISPR enzymes" refers to Class 2 CRISPR effector proteins including but not limited to Cas9, Cas12a (formerly known as Cpf1), Csn2, Cas4, C2c1, Cc3, Cas13a, Cas13b, Cas13c, Cas13d. In one embodiment, the CRISPR effector proteins described herein are preferably Cpf1 effector proteins.

As used herein, "guide RNA" or "gRNA" refers to the non-coding RNA sequence that binds to the complementary target DNA sequence to guide the CRISPR-Cas system in close contact with the target DNA strand.

As used herein, a "reporter molecule" refers to a single-stranded DNA or single-stranded RNA that is labeled with fluorescence and quencher, gold nanoparticles or biotin-FAM, and the dissociation of the reporter can be detected by either a fluorescence reader or colorimetric change in e.g., a paper lateral flow assay or spectrometer, and the like.

As used herein, the "target DNA fragment" is a portion of a MTB-specific DNA sequence. For example, IS6110 is an MTB complex-specific insertion sequence that is present in multiple copies per MTB genome. gryB mutation at positions 495, 516 and 533 have been reported to occur in fluoroquinolone-resistant MTB, and esxB is a CFT-10 protein secreted by MTB that contributes to the virulence thereof. Therefore, targeting these DNA fragments would facilitate the detection of MTB. Additional target DNA fragment can also be selected from the following MTB genes: rpoB, katG, inhA, rpsL, rrs, gyrA, gyrB, embB, eis and pncA.

As used herein, "DNA amplification" or "nucleic acid amplification" refers to natural and artificial processes by which the number of copies of a gene or a fragment of DNA is increased without a proportional increase in other genes.

As used herein, "polymerase chain reaction" or "PCR" refers to a method of amplifying a specific target region of a DNA strand by using a DNA polymerase and two primers (forward and reverse) that are complimentary to each end of the target region, along with dNTPs.

As used herein, "recombinase polymerase amplification" or RPA refers to a method of amplifying a specific target region using a recombinase, a single-stranded DNA-binding protein and strand-displacing polymerase. The recombinase pairs oligonucleotide primers with homologous sequence in duplex DNA, and the single-stranded DNA-binding protein binds to replaced strands of DNA to prevent the primers from being displaced. An optimal temperature at 37-42° C., the reaction progresses rapidly and results in specific DNA amplification without the need for thermal or chemical melting required by PCR.

As used herein, "nucleic acid sequence-based amplification" or NASBA refers to a primer-dependent method for continuously amplifying nucleic acids, particularly RNA sequences, in a single mixture at one temperature. Three enzymes are used: a reverse transcriptase, a RNase H, and T7 RNA polymerase. Two primers are used: the first primer includes a 3'-terminal sequence that is complementary to a target sequence and a 5'-terminal sense sequence of a promoter that is recognized by the T7 RNA polymerase; and the second primer includes a sequence complementary to the P1-primed DNA strand. First, an RNA template is given to the reaction mixture, where the first primer attaches to its complementary site at the 3' end of the template. The reverse transcriptase synthesizes the opposite, complementary DNA strand, extending the 3' end of the primer, moving upstream along the RNA template. At this time, RNAse H destroys the RNA template from the DNA-RNA compound (RNAse H only destroys RNA in RNA-DNA hybrids, but not single-stranded RNA). The second primer then attaches to the 5' end of the (antisense) DNA strand. Afterwards, the reverse transcriptase again synthesizes another DNA strand from the attached primer resulting in double stranded DNA, when the T7 RNA polymerase binds to the promoter region on the double strand. Since T7 RNA polymerase can only transcribe in the 3' to 5' direction, the sense DNA is transcribed and an anti-sense RNA is produced. This is repeated, and the polymerase continuously produces complementary RNA strands of the template which results in amplification.

Now a cyclic phase can begin similar to the previous steps. Here, however, the second primer first binds to the (−)RNA, and the reverse transcriptase now produces a (+)cDNA/(−)RNA duplex. RNAse H again degrades the RNA and the first primer binds to the now single stranded +(cDNA), followed by the reverse transcriptase producing the complementary (−)DNA and creating a dsDNA duplex. Lastly, the T7 polymerase binds to the promoter region, produces (−)RNA, and the cycle is complete.

As used herein, "rolling circle amplification" or RCA refers to an isothermal enzymatic process where a short DNA or RNA primer is amplified to form a long single stranded DNA or RNA using a circular DNA template and special DNA or RNA polymerases. The RCA product is a concatemer containing tens to hundreds of tandem repeats that are complementary to the circular template.

As used herein, "loop-mediated isothermal amplification" or LAMP refers to a single tube DNA amplification method, where the target sequence is amplified at a constant temperature of 60-65° C. using either two or three sets of primers and a polymerase with high strand displacement activity in addition to a replication activity. Typically, 4 different primers are used to amplify 6 distinct regions on the target gene, which increases specificity. An additional pair of "loop primers" can further accelerate the reaction.

As used here, "reporter molecule" refers to a molecule having nucleotides linked to a detectable reporter group, such that when the nucleotides hybridize with a matching sequence, the reporter group produces detectable signals. Non-limiting reporter molecule includes a single-stranded DNA or RNA labeled with fluorescence and quencher, gold nanoparticles, biotin-FAM.

As used herein, "anti-human DNA antibodies" refers to anti-nuclear antibodies that target double stranded human DNA as antigen.

As used herein, "anti-MTB antibodies" refers to antibodies that target *Mycobacterium tuberculosis* DNA due to its specific methylation pattern.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| CRISPR | Clustered regularly interspaced short palindromic repeats |
| gRNA | Guide RNA |
| LAMP | Loop-mediated isothermal amplification |
| MTB | *Mycobacterium tuberculosis* |
| NASBA | Nucleic acid sequence-based amplification |
| PAM | Protospacer adjacent motif |
| PCR | Polymerase chain reaction |
| RCA | Rolling circle amplification |
| EV | Extracellular vesicle |
| NTM | Non-tuberculosis mycobacteria |

BRIEF DESCRIPTION OF THE DRAWINGS

FIG. 1. Illustration of the method of this disclosure.

FIG. 2. Fluorescent results of the serum samples.

DETAILED DESCRIPTION

The disclosure provides novel method of detecting MTB DNA in a serum sample. The method comprises the steps of:

a) extracting nucleic acids from a serum sample; b) amplifying a target nucleic acid sequence, and c) detecting presence of the target nucleic acid sequence using a CRISPR-mediated system, wherein the CRISPR-mediated system comprises a CRISPR effector protein, a guide RNA that hybridizes with the target nucleic acid sequence, and a reporter molecule.

Primers used in the DNA amplification step are designed to amplify only the MTB gene sequences that are conserved across *Mycobacterium* species or have been reported for certain drug resistance. For example, IS6110 is an MTB-specific insertion sequence. Other MTB-specific genes can also be amplified, such as esxB, rpoB, katG, inhA, rpsL, rrs, gyrA, gyrB, embB, eis and pncA.

The DNA sequence of *M. tuberculosis* IS6110 can be found at Accession Number X17348.1. The DNA sequence of *M. tuberculosis* esxB from strain H37Rv can be found at AL123456.3 (4352274-4352576). The DNA sequence of *M. tuberculosis* gryB from strain H37Rv can be found at AL123456.3 (5240-7267). In designing the primers, the focus is on amplifying the PAM recognizable by the CRISPR effector protein.

The gRNA sequences were designed in accordance with the target fragments and the primers used in the DNA amplification step. In other words, the gRNA sequences are portions of the IS6110, IS986, esxB, gryB, rpoB, katG, inhA, rpsL, rrs, gyrA, gyrB, embB, eis or pncA. These genes are listed in Table 1.

TABLE 1

Candidate gene information for TB detection

| No. | Target Gene | Function | Reference |
|---|---|---|---|
| 1 | IS6110 | IS6110 is an insertion element of the *M. tuberculosis* complex | ncbi.nlm.nih.gov/nuccore/X17348.1?report=fasta |
| 2 | IS986 | IS986 belongs to the IS3-like family of insertion sequences of *M. tuberculosis* | ncbi.nlm.nih.gov/pmc/articles/PMC268102/ |
| 3 | exsB | Coding gene of ESAT-6 and CFP-10 | ncbi.nlm.nih.gov/gene?Db=gene&Cmd=ShowDetailView&TermToSearch=886194&itool=EntrezSystem2.PEntrez.Gene.Gene_ResultsPanel.Gene_RVDocSum |
| 4 | rpoB | Rifampin resistance relates gene of *M. tuberculosis* | ncbi.nlm.nih.gov/pubmed/8031050 |
| 5 | katG | Isoniazid resistance relates gene of *M. tuberculosis* | ncbi.nlm.nih.gov/pmc/articles/PMC500838/ |
| 6 | inhA | Isoniazid and ethionamide resistance relate gene of *M. tuberculosis* | ncbi.nlm.nih.gov/pubmed/8284673 |
| 7 | rpsL | Streptomycin resistance relates gene of *M. tuberculosis* | ncbi.nlm.nih.gov/pubmed/7968530 |
| 8 | rrs | Streptomycin and Kanamycin resistance relate gene of *M. tuberculosis* | ncbi.nlm.nih.gov/pmc/articles/PMC88513/ |
| 9 | gryA | Fluoroquinolone resistance relates gene of *M. tuberculosis* | ncbi.nlm.nih.gov/pubmed/22552454 |
| 10 | gryB | Fluoroquinolone resistance relates gene of *M. tuberculosis* | ncbi.nlm.nih.gov/pubmed/22552454 |
| 11 | embB | Ethambutol resistance relates gene of *M. tuberculosis* | aac.asm.org/content/53/3/1061 |
| 12 | eis | Kanamycin resistance relates gene of *M. tuberculosis* | ncbi.nlm.nih.gov/pubmed/22593564 |
| 13 | pncA | Pyrazinamide resistance relates gene of *M. tuberculosis* | ncbi.nlm.nih.gov/pmc/articles/PMC2346646/ |

The present invention is exemplified with respect to IS6110, esxB, gryB as the target fragment. However, these targets are exemplary only, and the invention can be broadly applied to other conserved regions among *Mycobacterium* species. The following examples are intended to be illustrative only, and not unduly limit the scope of the appended claims.

Example 1

Four samples were collected/prepared as follows. The method of this disclosure was performed on all four samples.

| Sample No. | Information | TB Status |
|---|---|---|
| 1 | Healthy human serum spiked with 100 copies of IS6110/esxB/gryB fragments | Positive |
| 2 | Healthy human serum spiked 10 ng of genomic DNA of MTB-H37RV | Positive |
| 3 | Healthy human serum 1 | Negative |
| 4 | Healthy human serum 2 | Negative |
| 5 | Healthy human serum 3 | Negative |
| 6 | Healthy human serum 4 | Negative |
| 7 | Healthy human serum 5 | Negative |
| 8 | Healthy human serum 6 | Negative |
| 9 | Healthy human serum 7 | Negative |
| 10 | Clinical TB-positive sample 1 | Positive |
| 11 | Clinical TB-positive sample 2 | Positive |
| 12 | Clinical TB-positive sample 3 | Positive |
| 13 | Clinical TB-positive sample 4 | Positive |
| 14 | Clinical TB-positive sample 5 | Positive |

1. Extracting DNA

To extract DNA from a serum sample, the following materials were used: Quick-cfDNA™ Serum & Plasma Kit (D4076) that contains S&P 5× Digestion Buffer, Proteinase K, S&P DNA Binding Buffer, Zymo-Spin™ III-S Column Assembly, S&P DNA Prep Wash Buffer, S&P DNA Wash Buffer, DNA Elution Buffer (10 nM Tris-HCL, pH 8.5, 0.1 mM EDTA), and 1.5 mL Tube.

If the serum sample is stored in −80° C., first place the sample at room temperature to thaw for 30 minutes. 100 μl of the thawed serum was mixed with 25 μl of S&P 5× Digestion Buffer and 10 μl of Proteinase K in a DNA Low Binding Tube.

Subsequently, the mixture was incubated at 55° C. for 30 minutes for digestion, followed by the addition of two volumes of S&P DNA Binding Buffer to the digested samples and mixed thoroughly.

The entire mixture was then transferred into Zymo-Spin™ III-S Column Assembly in a 1.5 ml tube, and centrifuged at 1000 g for 2 minutes. The flow-through was discarded.

400 μl of S&P DNA Prep Buffer was added to the column and centrifuged at ≥10000 g for 30 seconds, and the flow-through was discarded. The column was washed twice with 400 μl of S&P Wash Buffer, each centrifuged at ≥10000 g for 1 minute.

The column was then transferred into a 1.5 ml DNase-free tube. 40 μl of DNA Elution Buffer was added directly to the column matrix and incubated at room temperature for 3 minutes, followed by centrifugation at maximum speed for 30 seconds. The collected DNA was then stored at −20° C. until further use.

2. Amplifying DNA

PCR was performed as an example of DNA amplification, and as discussed above, other DNA amplification techniques can be used. To perform PCR, the following materials were used: DEPC-Treated Water (1907041), Primer F and Primer R (List in the following table), 10×DNA Polymerase PCR Buffer, and DNA polymerase (such as AccuPrime™ Taq DNA Polymerase System).

Three pairs of primers were designed to amplify IS6110, esxB and gryB of MTB genome. The reason for choosing IS6110, as discussed above, is because the MTB genome has multiple copies thereof that could increase sensitivity. Primers against esxB was designed because of esxB is conserved across different *Mycobacterium* species. Primers against gryB was designed specifically to detect whether the MTB is fluoroquinolone-resistant. The designed primers used in this step is listed below:

TABLE 2

PCR PRIMERS

| Target Gene | Name | Sequence (5'-3') |
|---|---|---|
| IS6110 | SEQ ID NO. 1(F) | GGTCGGAAGCTCCTATGACAATGCACTAGCC |
| | SEQ ID NO. 2(R) | TTGAGCGTAGTAGGCAGCCTCGAGTTCGAC |
| esxB | SEQ ID NO. 3(F) | TAAAGAGAGAAAGTAGTCCAGCATGGCAGAG |
| | SEQ ID NO. 4(R) | TCTCGTCGAGTTCCTGCTTCTGCTTATTGG |
| gryB | SEQ ID NO. 5(F) | CTGTTGTTGACGTTGTTGTTCCGGTTCATGC |
| | SEQ ID NO. 6(R) | CTGAATGCCGTCTTCCTTGTTGATCTTCTTC |

The following components were added to a sterile thin walled 0.2 ml PCR tube at room temperature:

| Components | Amount (μl) | Component | Amount (μl) |
|---|---|---|---|
| DEPC-treated water | 15.12 | Primer R | 0.4 |
| 10X DNA Polymerase PCR buffer with hybridization enhancer component | 2 | AccuPrime ™ Taq DNA Polymerase system | 0.08 |
| Primer F | 0.4 | Extracted DNA | 2 |

The content in the tubes was mixed well, and centrifuged briefly to collect the content. The tubes were incubated in a thermal cycler at 95° C. for 2 minutes to completely denature the DNA template and activate the enzyme.

35 cycles of PCR amplification were then performed as follows: denature: 95° C. for 30 seconds; anneal: 60° C. for 30 seconds; extend: 72° C. for 30 seconds. After completion of 35 cycles, the temperature of the reaction mixture was maintained at 4° C. The resulting PCR products was then stored at −20° C. until next step.

3. Crispr Detection

After the amplification step, MTB detection with CRISPR-Cas system was performed with the following materials: DEPC-Treated Water (1907041), EnGen® Lba Cas12a (Cpf1), a buffer solution that comprises NaCl/Tris-HCl/MgCl2/BSA (10×NEBuffer™ 2.1), gRNA (list in the following table), Fluorescent Reporter (5-6-FAM-TTTTTTTTTTTT-BHQ1), and Corning® 96 Well Half-Area Microplate.

As discussed above, the gRNA sequences were designed in accordance with the target fragments and PCR primers, and are listed below:

TABLE 3 gRNA sequence

| Target Gene | Name | Sequence (5'-3') |
|---|---|---|
| IS6110 | SEQ ID NO. 7 | UAAUUUCUACUCUUGUAGAUAUCAGCUCGGUCUUGAAUAG |
| esxB | SEQ ID NO. 8 | UAAUUUCUACUCUUGUAGAUGAGCGGAUCUCCGGCGACCU |
| gryB | SEQ ID NO. 9 | UAAUUUCUACUCUUGUAGAUGCACAACCGCCGCUGUACAA |

To carry out the CRISPR detection step, the following components were added to a Half-area Microplate well, mixed well and incubated at room temperature for 10 minutes:

| Components | Amount (μl) | Component | Amount (μl) |
|---|---|---|---|
| DEPC-treated water | 1.5 | 1 μM EnGen ® Lba Cas12a | 1 |
| 10X NEBuffer ™ 2.1 | 3 | 2 μM Fluorescent reporter | 1.5 |
| 300 nM gRNA | 3 | PCR product | 20 μL |

It is noted that the PCR product with the buffer solution mixture was added to the CRISPR detection mixture, as opposed to separating the PCR product from the buffer solution. This also increases the detection sensitivity.

The system was incubated in the dark at 37° C. for 20 minutes with vibration. The fluorescent signal was measured with a plate reader. The result is shown in FIG. 2. When the sample produces signal intensity two times higher than that of the negative control, it is defined as positive. As can be seen in FIG. 2, positive samples 1, 2, and 4 show fluorescent intensity comparable to the positive control, whereas negative sample 3 shows fluorescent intensity comparable to the negative control.

Prophetic Example 1

To obtain best results, the ratio of (Cas12a:gRNA:reporter molecule) in the CRISPR detection step is varied, otherwise the DNA extraction, DNA amplification and CRISPR detection steps are the same as Example 1. This optimized ratio will further improve the specificity and sensitivity of this method.

Prophetic Example 2

To further improve the sensitivity of this method, MTB-DNA enriching and/or human-DNA depletion from the serum sample will be performed prior to the DNA amplification step. Human DNA has a specific methylation pattern that serves as the epitope of anti-human DNA antibodies. By treating the extracted DNA with the anti-human DNA antibodies to deplete human DNA in the serum sample, it is expected to further improve the sensitivity of the method of this disclosure.

Similarly, MTB DNA has its own specific methylation patterns that are lineage- or species-specific, and can serve as epitopes for anti-MTB antibodies. Therefore, by treating the serum sample with anti-MTB antibodies to capture only MTB DNA fragments, the sensitivity of this method can be further improved.

The following references are incorporated by reference in their entirety for all purposes.

What is claimed is:

1. A method of detecting *Mycobacterium tuberculosis* (MTB) in a bodily fluid sample, comprising the steps of:

a) amplifying an MTB target nucleic acid sequence from cell-free DNA in a bodily fluid sample; and b) detecting presence of the MTB target nucleic acid sequence using a CRISPR-mediated system;

wherein said CRISPR-mediated system comprises a CRISPR effector protein, a guide RNA (gRNA) that hybridizes with the MTB target nucleic acid fragment, and a reporter molecule that is detectable on cleavage by said CRISPR effector protein, wherein the gRNA has at least one of the following sequences: SEQ ID NO. 7, SEQ ID NO. 8, or SEQ ID NO. 9.

2. The method of claim 1, further comprises, prior to step a), the following step:

a-1) extracting nucleic acids from the bodily fluid sample.

3. The method of claim 1, wherein the target nucleic acid fragment is DNA.

4. The method of claim 2, wherein in step a-1) the extracting step further comprises:

a-2) depleting human DNA using anti-human DNA antibodies.

5. The method of claim 2, wherein in step a-1) the extracting step further comprises:

a-3) enriching MTB bacterial DNA by using anti-MTB antibodies.

6. The method of claim 2, wherein in step a-1) the extracting step further comprises:

a-4) isolating extracellular vesicles by at least one of: ultracentrifugation, size exclusion chromatography, polymer precipitation, membrane filtration or membrane affinity isolation.

7. The method of claim 3, wherein step a) is carried out using polymerase chain reaction (PCR), recombinase polymerase amplification (RPA), nucleic acid sequence-based amplification (NASBA), rolling circle amplification (RCA), or loop-mediated isothermal amplification (LAMP).

8. The method of claim 7, wherein step a) is carried out using PCR.

9. The method of claim 8, wherein a hybridization enhancer is used in the PCR, and the hybridization enhancer is transferred into the detecting step b).

10. The method of claim 1, wherein in step b) the CRISPR effector protein is selected from a group consisting of Casl2a, Cas9 and Cas13.

11. The method of claim 1, wherein the reporter molecule is a single-stranded DNA or a single-stranded RNA labeled with fluorescence and quencher, gold nanoparticles, or biotin-FAM.

12. The method of claim 11, wherein the reporter molecule is 5'-6-FAM-TTTTTTTTTTTT-BHQ1.

13. The method of claim 1, wherein said bodily fluid sample is obtained from serum, plasma, or urine.

14. The method of claim 2, wherein in step a) is carried out in room temperature.

15. The method of claim 2, wherein the target DNA sequence is a portion of IS6110, IS986, esxB, gryB, rpoB, katG, inhA, rpsL, rrs, gyrA, gyrB, embB, eis and pncA.

16. The method of claim 2, wherein a pair of primers are used in step b) for the DNA amplification, wherein the primers are SEQ ID NOs. 1 and 2.

17. The method of claim 2, wherein a pair of primers are used in step b) for the DNA amplification, wherein the primers are SEQ ID NOs. 3 and 4.

18. The method of claim 2, wherein a pair of primers are used in step b) for the DNA amplification, wherein the primers are SEQ ID NOs. 5 and 6.

19. A method of detecting *Mycobacterium tuberculosis* (MTB) in a serum sample, comprising the steps of:

a) extracting DNA from a serum sample to produce a DNA sample;

b) amplifying an MTB target DNA sequence from said DNA sample using PCR or RPA to produce an amplified DNA, wherein a pair of primers are used, and wherein the primers are SEQ ID NOs. 1&2, 3&4 or 5&6; and c) detecting presence of the MTB target DNA fragment in said amplified DNA using a CRISPR-mediated system;

wherein said CRISPR-mediated system comprises Casl2a, a guide RNA (gRNA), and a reporter molecule that is detectable on cleavage by Casl2a, wherein the gRNA is SEQ ID NO. 7, 8 or 9.

20. The method of claim 19, wherein in step a) the extracting step further comprising at least one of:

a-1) depleting human DNA from said serum sample or said DNA sample using anti-human DNA antibodies, a-2) enriching MTB bacterial DNA from said serum sample or said DNA sample by using anti-MTB antibodies, or a-3) isolating extracellular vesicles by at least one of: ultracentrifugation, size exclusion chromatography, polymer precipitation, membrane filtration or membrane affinity isolation.

* * * * *